United States Patent
Dirac et al.

(10) Patent No.: US 7,248,906 B2
(45) Date of Patent: Jul. 24, 2007

(54) METHOD AND DEVICE FOR MONITORING ANALYTE CONCENTRATION BY OPTICAL DETECTION

(75) Inventors: Holger Dirac, Birkeroed (DK); Kasper Oktavio Schweitz, Hilleroed (DK)

(73) Assignee: Danfoss A/S, Nordborg (DK)

( * ) Notice: Subject to any disclaimer, the term of this patent is extended or adjusted under 35 U.S.C. 154(b) by 278 days.

(21) Appl. No.: 10/499,596

(22) PCT Filed: Dec. 12, 2002

(86) PCT No.: PCT/EP02/14141

§ 371 (c)(1),
(2), (4) Date: Nov. 19, 2004

(87) PCT Pub. No.: WO03/051191

PCT Pub. Date: Jun. 26, 2003

(65) Prior Publication Data

US 2005/0070770 A1    Mar. 31, 2005

(30) Foreign Application Priority Data

Dec. 17, 2001 (DK) ............... 2001 01892
Dec. 17, 2001 (DK) ............... 2001 01904
Feb. 14, 2002 (DK) ............... 2002 00224

(51) Int. Cl.
*A61B 5/00* (2006.01)

(52) U.S. Cl. ............ 600/316; 600/310; 600/341
(58) Field of Classification Search ........... 600/310, 600/316, 322, 327, 341
See application file for complete search history.

(56) References Cited

U.S. PATENT DOCUMENTS 5,353,792 A * 10/1994 Lubbers et al. ............ 600/311
5,372,135 A    12/1994 Mendelson et al.
5,833,603 A * 11/1998 Kovacs et al. ............ 600/317
6,011,984 A    1/2000 Van Antwerp et al.

(Continued)

FOREIGN PATENT DOCUMENTS

WO    WO 00/32102    6/2000

(Continued)

OTHER PUBLICATIONS

P R Troyk et al., "Inductive links and drivers for remotely-powered telemetry systems", Illinois Instritute of Technology, pp. 60-62.

(Continued)

*Primary Examiner*—Eric F. Winakur
(74) *Attorney, Agent, or Firm*—McCormick, Paulding & Huber LLP

(57) ABSTRACT

A method and device are provided for the determination of the concentration of compounds in body tissue. The method utilises optical methods based on the interaction of light with compounds, whereby the concentration of the compound under analysis is determined. The method is especially suited for analysis for the concentration of glucose in blood or tissue of diabetic patients, a device being implanted underneath the skin of the patient and the method being carried out by using the implanted device. The device contains photo detectors at different levels connected by wires to an electronic circuit device. A differential analysis is performed on the signals from the detectors to reduce the effect of skin on the analysis.

20 Claims, 4 Drawing Sheets

U.S. PATENT DOCUMENTS 6,122,536 A * 9/2000 Sun et al. .................. 600/341
2002/0161286 A1 10/2002 Gerber et al.
2003/0050542 A1 3/2003 Reihl et al.

FOREIGN PATENT DOCUMENTS

WO  WO 00/33065  6/2000
WO  WO 01/66005  9/2001

OTHER PUBLICATIONS

J Tenhunen et al., "Non-invasive glucose measurement based on selective near infrared absorption; requirements on instrumentation and spectral range", Measurement 24 (1988), VTT Electronics, pp. 173-177.

M Cope et al., "Non-invasive Measurement of Tissue Oxygenation using Near Infrared (NIR) Spectroscopy", Dept. of Medical Physics & Bioengineering, University College London, pp. 14/1-14/4.

Z Tang et al., "Data Transmission from an Implantable Biotelemeter by Load-Shift Keying Using Circuit Configuration Modulator", IEEE Transactions on Biomedical Engineering, vol. 42, No. 5, May 1995, pp. 524-528.

W Cheong et Al., "A Review of the Optical Properties of Biological Tissue", IEEE Journal of Quantum Electronics, vol. 26, No. 12, Dec. 1990, pp. 2166-2185.

R Arnold et al., "An Implantable Low Power Mixed Signal Telemetry Chip for Measurements of the Frequency Dependent Impedance of Transplanted Kidneys for Rejection Control", Technical University Berlin, Insttitute for Microelectronics, P3-P6.

D K Buslov et al., "Analysis of the results of a-D glucose Fourier transform Infrared spectrum deconvolution: comparison with experimental and theoretical data", Spectrochimica Acta Part A 55 (1999), pp. 229-238.

P R Troyk et al., "Closed-Loop Class E Transcutaneous Power and Data Link fr MicroImplants", IEEE Transactions on Biomedical Engineering, vol. 39, No. 6, Jun. 1992, pp. 589-599.

A Gowda et al., "Development of an inplantable skin port sensor for use as an in vivo optical glucose sensing platform", BioTex, Inc et al., Optical Diagnostics and Sensing of Biological Fluids and Glucose and Cholesterol Monitoring, Proceedings of SPIE, vol. 4263 (2001) , pp. 11-19.

* cited by examiner

METHOD AND DEVICE FOR MONITORING ANALYTE CONCENTRATION BY OPTICAL DETECTION

CROSS-REFERENCE TO RELATED APPLICATIONS

This application is entitled to the benefit of and incorporates by reference essential subject matter disclosed in International Application No. PCT/EP02/14141 filed on Dec. 12, 2002; Danish Patent Application No. PA 2001 01892 filed on Dec. 17, 2001; Danish Patent Application No. PA 2001 01904 filed on Dec. 17, 2001; and Danish Patent Application No. PA 2002 00224 filed on Feb. 14, 2002.

FIELD OF THE INVENTION

This invention relates to biological sensors, more specifically to implantable sensors for optically detecting compounds such as glucose, in a living creature, for example, in the human or animal body. More specifically, but not exclusively, this invention relates to biological sensors for the detection of glucose in blood or tissue of a diabetic patient.

BACKGROUND OF THE INVENTION

Diabetic patients can improve their life quality and life expectancy by maintaining their blood glucose concentration close to the natural level of a healthy person. To achieve this natural concentration, diabetic patients must frequently measure their glucose concentration, and adjust their insulin dosing in accordance with the measured concentration. Usually, a blood sample is obtained for measurement of blood glucose concentration, and there are a number of different glucose test kits on the market based on measurement from a blood sample. The disadvantage of these test kits is the need to take a blood sample which must be collected from a suitable place in the body.

Self monitoring devices, based on capillary blood glucose, are practical but still require repeated and frequent skin punctures, which is inconvenient for the patient and require certain hygienic precautions.

Biological sensors in the form of implantable devices are also known in the art and include electrochemical devices and optical devices based on the creation of an electrical or optical signal by the consumption of the compound detected by the analysis. An example is to be found in U.S. Pat. No. 6,011,984, which discloses methods utilising an amplification component. The sensitivity and the responsivity of such devices are influenced by the formation of a bio film, for example, by fibrous encapsulation of the device which reduces the transport rate of the compound to the sensor. Depending on the specific sensor, other mechanisms which cause deterioration of sensor performance of implanted devices, may also be present, for example, membrane delamination and degradation, enzyme degradation and electrode passivation.

Various proposals have been made for non-invasive measurement of glucose levels in the human body by spectroscopic methods but the effects of water in the body, the low concentration of glucose to be measured and the optical effects produced by skin all contribute to the difficulty of making satisfactory measurements.

One solution proposed (Gowda et al Proc. SPIE Vol. 4263 (2001) p. 11 et seq) has been to provide an implanted window in the skin but, leaving aside any other considerations, some patients, at least, would find this unpleasant.

Another solution (U.S. Pat. No. 5,372,135) is to perform the analysis through the ear lobe and perform a computer analysis on results before and after the volume of the blood in the tissue has been changed. This technique has the disadvantage that the skin has an effect both on the entry and the exit of light.

It is an object of the invention to provide an implantable device which can be used for monitoring analyte concentration but enables the effects of skin in the analysis to be reduced.

SUMMARY OF THE INVENTION

The present invention provides a device for implantation beneath the skin of a living creature, the device having outer surfaces of biocompatible material and comprising:

detection means for detection of light, the said detection means comprising at least one substantially flat area constituting a first area or, when a plurality of areas are provided, a first group of areas and at least one substantially flat area constituting a second area or, when a plurality of areas are provided, a second group of areas; and transmitting means for transmitting a signal derived from said detection means to an external device, wherein the arrangement of the first and second areas or groups of areas within the device is such that the distance, between the skin and said detection means, over which light from a light source interacts with compounds and tissue in respect of said first area or group of areas differs from the distance, between the skin and said detection means, over which light from the light source interacts with compounds and tissue in respect of said second area or group of areas.

The difference between the said distances allows a differential analysis to take place so that the effects of skin in the results can be reduced or avoided. The differential analysis may be a simple formation of a difference in signals or may be a complex computer correlation. The analysis may be performed within the device or externally.

Such a device can be used to provide an alternative way to overcome the discomfort and inconvenience for diabetic patients, by providing (once the initial implantation is finished) a non-invasive measurement method for glucose concentration.

The implanted detector may be divided into areas at different levels. By this means, the distance travelled by the light through the compound of interest in the body tissues, and thus the interaction of light with the compound, varies from area to area.

The spacing between the different levels may, for example, be between 0.5 and 5 millimetres, for example, between 0.5 and 3 millimetres, for example between 1 and 2.5 millimetres.

The number of areas within a group may, for example, be between 2 and 30, for example, between 5 and 25, for example, between 10 and 20.

The device may include means to provide a differential analysis of signals arising from the said difference in distances. Instead, a differential analysis may be performed on the data in an external apparatus to which the device transmits data.

Heating means and/or cooling means may be provided to act on the body region surrounding the device.

The areas may be provided within wells to reduce the effects of stray light.

The areas may be covered by optical filter means to prevent light of wavelengths other than those of interest from reaching the areas.

Preferably, groups of areas are provided, each group of areas forms a common level, and the common levels have a predetermined spacing from each other to provide the said difference in distance over which light interacts with compounds and tissue.

Preferably, the first group of areas is formed at a base level of the device and the second group of areas is formed by projections from the said base level to a top level.

Preferably, the device further includes a spacer covering one of said at least one areas or groups so that compounds and tissue are unable to fill the volume of the spacer, the spacer providing the difference in distance over which light interacts with compounds and tissue.

The spacer can be formed by a sealed volume above some of the areas so that light reaching those areas experiences less interaction with the compound and tissues than light reaching uncovered reflecting areas.

At least one substantially flat area constituting a third area or group of areas may be provided and form a common level between the base level and the top level.

At least a part of one of said areas may be formed by a permeable membrane.

The said membrane may be permeable to glucose.

The invention also provides a method for optically detecting the content of a compound in the body of a living creature, the method comprising:

directing a light source on different areas of an implanted device containing detection means, the distance, between the skin and said detection means, over which light from a light source interacts with compounds and tissue in respect of one area differing from the distance, between the skin and said detection means, over which light from a light source interacts with compounds and tissue in respect of another area;

obtaining light-representing signals by means of said detection means; and analysing the detected signals, the analysis preferably being based on the difference between the detected signals, to obtain a value for the content of a compound being detected.

In another aspect, the invention provides a method for optically detecting the content of a compound in the body of a living creature, the method comprising:

directing a light source on different areas of an implanted device containing detection means;

obtaining light-representing signals by means of said detection means;

transmitting said light-representing signals to an external device; and analysing the detected signals to obtain a value for the content of the compound being detected.

Such methods allow non-invasive measurement after the initial implantation in which the influence of bio fouling on the value of the measured signal is decreased.

Preferably, the analysis of the detected signals is a differential analysis.

The compound may be glucose.

The measuring principle used in this invention is not, however, limited to implanted devices in diabetic patients for measuring glucose concentration, but can be used in many other applications. The basic principle can be used for measuring compounds in locations which are difficult to access, and where the physical and chemical conditions vary over time. Measurement can be made of glucose concentration in a bioreactor, glucose in fruit juice etc.

The invention also provides a device for implantation beneath the skin of a living creature, the device having outer surfaces of biocompatible material and comprising:

reflection means for reflection of light, the said reflection means comprising at least one substantially flat area constituting a first area or, when a plurality of areas are provided, a first group of areas and at least one substantially flat area constituting a second area or, when a plurality of areas are provided, a second group of areas; and wherein the arrangement of the first and second areas or groups of areas within the device is such that the distance, between the skin and said reflection means, over which light from a light source interacts with compounds and tissue in respect of said first area or group of areas differs from the distance, between the skin and said reflection means, over which light from the light source interacts with compounds and tissue in respect of said second area or group of areas.

BRIEF DESCRIPTION OF THE DRAWINGS

Implantable devices constructed in accordance with the invention and methods in accordance with the invention will now be described, by way of example only, with reference to the accompanying drawings, in which.

DETAILED DESCRIPTION OF THE PREFERRED EMBODIMENTS

In the illustrated embodiments of the invention, optical methods based on the interaction of light with compounds and body tissues are utilised. The optical methods in their general aspects correspond to those described in the literature, for example, using Beer-Lambert law and/or radiative transport theory and will not therefore be described further here.

In the illustrated embodiments of the invention, light from a light source is incident on an implanted detector, the light is detected by a detection device in the implanted detector, and a signal is transmitted to a receiving device for analysis. The characteristics of the detected light depend on the interaction with the compounds encountered on the way from the light source to the detector.

In the illustrated embodiments of the invention, the implanted detector is divided into areas at different levels, so that the distance for the light through the compounds, and thus the interaction with light, varies from area to area. A differential analysis is performed on signals produced by the detector.

Figure 1:
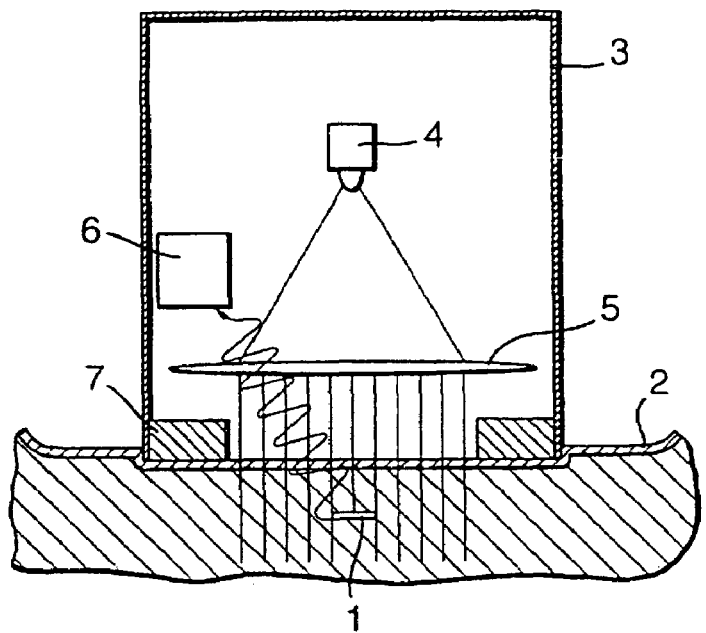
FIG. 1 is a schematic representation showing an optical device, an implanted device and a receiving device.

Referring now to FIG. 1, an implanted device 1 is placed underneath the skin 2 so that the compound to be measured is contained between the skin and the implanted device. An optical device 3, containing a light source 30 and a lens system 5, is placed external to the skin above the implanted device, and a signal for the detected light is transferred from the implanted device to a receiver 6.

The light intensity emitted from the light source is preferably approximately constant over the whole of the implanted device. It is thereby ensured that variations in the detected light are due only to absorption in the path from light source to detector and not due to variations in emitted light intensity.

Referring still to FIG. 1, the light source is, for example, a light source of a broad continuous spectrum, for example a thermal white light source, depending on the compound to be measured. In the case of measuring glucose concentration, the wavelength should be well represented in the near infrared spectrum, more specifically between 1000 and 2500 nm. The light source is in this case therefore, for example, an LED, one or more laser diodes or an LED array producing wavelengths in this range. Alternatively a monochromator can be used with a white light source to select light within a desired wavelength range and directed onto the implanted device.

Wavelength specific light detection can also be obtained by covering the detectors with a film, transparent for only a specific wavelength or wavelength range. In this way is it possible to detect within a range of wavelengths simply by having a light source with a range of wavelengths and a number of detectors with different films. The film covering each detector also prevents detection of background light, as this not will pass through the film. Alternatively the detection within a range of wavelengths can be carried out by having more than one light source, and successively directing light of different wavelengths on the implanted device.

The light absorption for some compounds is temperature dependent, meaning that the detected light on the implanted device varies with the temperature of the compounds and tissue. FIG. 1 shows a cooling/heating device 7, such as a Pelletier element, formed as a ring around the light emitting area. With this element it is possible to perform measurements at different temperatures, so as to facilitate and improve the analysis. In case of analysis at different temperatures, the actual temperature can be recorded by a thermo element or the like, placed in the device 3.

Figure 8:
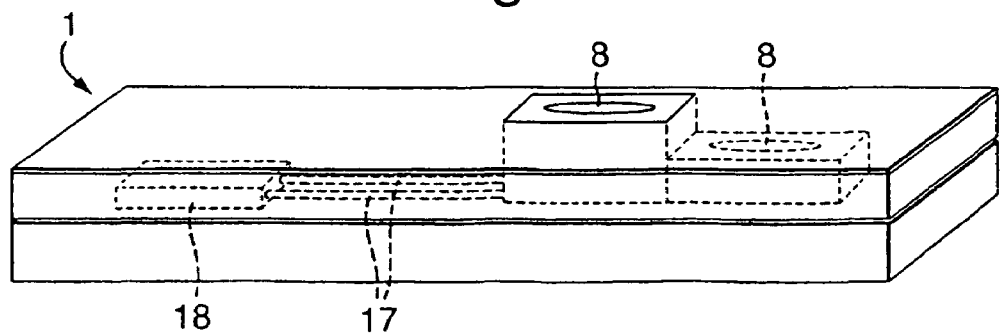
FIG. 8 is a schematic representation of a seventh implantable device embodying the invention, the device including electric connections and an electronic circuit device.

Referring to FIG. 8, the implanted device 1 contains a number of photo detectors 8, which by wires 17 are connected to an electronic circuit device 18. The electronic circuit device can be operated by power and data transmission without the use of connecting wires to the outside. Such power transmission can be implemented by the use of a so-called inductive link, which is basically a coreless transformer. Transmission of data from the electronic circuit device to the external receiver can take place, for example, by varying the load seen by the secondary of the transformer located in the implanted device (for example, the resistance change of a photo conductivity cell), or, for example, by measuring the change of resonance frequency of a series resonant circuit (for example, the change of capacitance due to the photo current in a photo diode).

Figure 2:
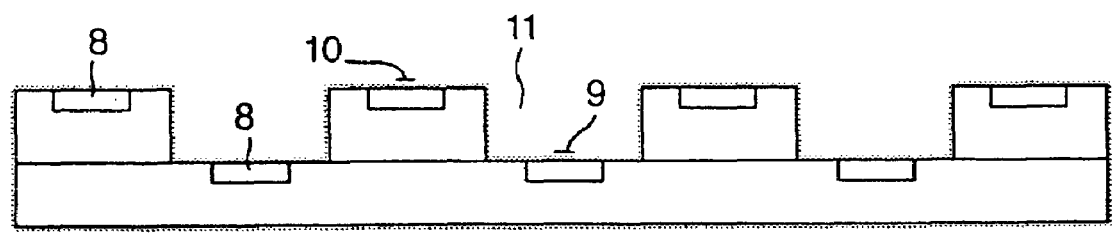
FIG. 2 is a schematic representation of a first implantable device embodying the invention, the device containing photo detectors and being coated with a biocompatible material.

Referring now to FIG. 2, the implanted device shown here consists of a number of detectors 8, contained in a polymeric or elastomeric matrix with biocompatible surfaces. The shape of the detector is made step-like to provide two levels of detection areas, base level 9 and extended level 10. In this way the detected light varies depending on which level the light is detected in, and the variation is dependent on the interaction of light with compounds and components in the volume between the two levels, henceforth called the measurement volume 11.

Figure 3:
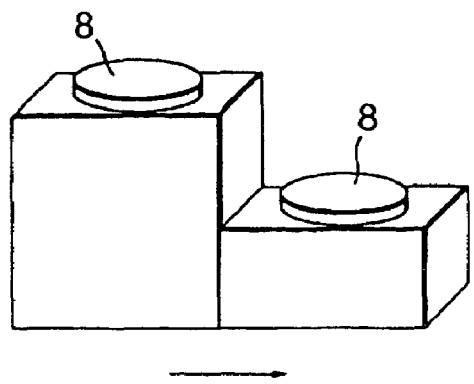
FIG. 3 is a schematic representation of a second implantable device embodying the invention, the device being step-like and having two detector levels.
Figure 4:
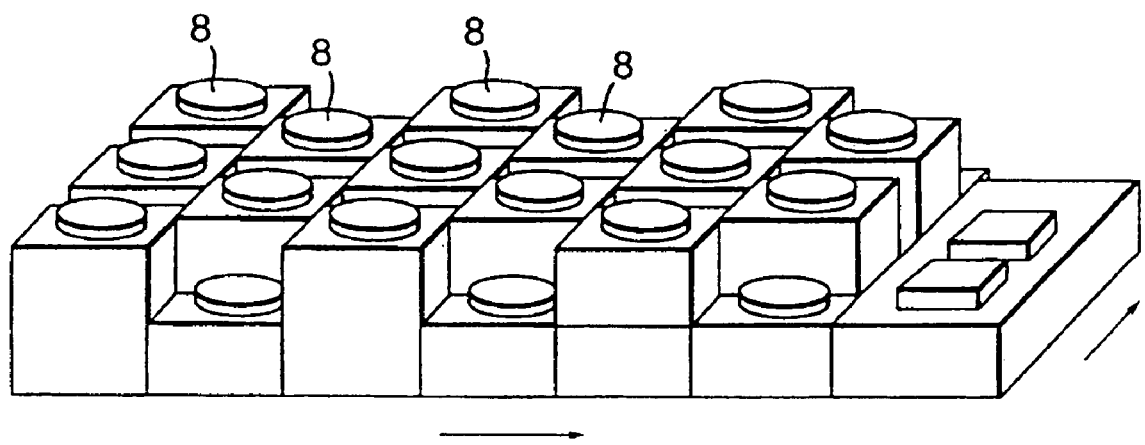
FIG. 4 is a schematic representation of a third implantable device embodying the invention, the device containing a multiplicity of detection areas at two different levels.

The implanted device can, for example, have a step-like shape in one direction, as indicated by an arrow in FIG. 3, or a step-like shape in two directions as indicated by two arrows in FIG. 4. Having more than one detector at each level increases the sensitivity of the analysis, as the signals from each level can then be averaged.

Figure 5:
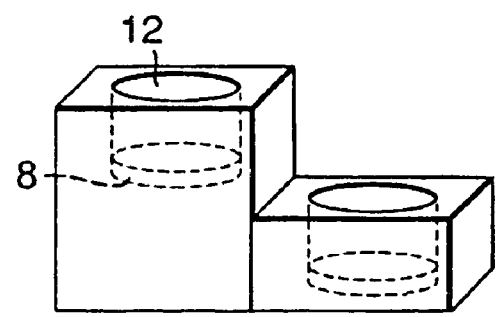
FIG. 5 is a schematic representation of a fourth implantable device embodying the invention, the device having photo detectors placed in detector wells.
Figure 6:
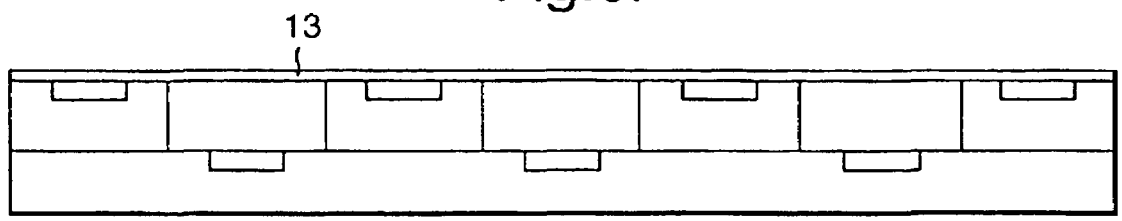
FIG. 6 is a schematic representation of a fifth implantable device embodying the invention, the device having detection areas covered by a membrane on the top.

Referring now to FIG. 5, each detector is shown placed in a detection well 12 so that only parallel light is detected. This has the effect that only the emitted and directly transmitted light is detected and not light from another light source, such as background light.

Covering the device with a membrane 13 can reduce interference by other compounds and noise due to scattering components. The membrane is sufficiently transparent at the appropriate wavelengths employed for the measurement (if placed on top of the measurement volume), and is permeable to the compound to be measured, for example glucose, but prevents other molecules larger than the compound to be measured from entering the measurement volume. The membrane can be placed above the measurement volumes, that is, between measurement volumes and the light source and detector, and/or to the sides of the measurement volumes. Placing the membrane to the side of the measurement volume enables a long optical path length and at the same time a relatively short response time of the device with respect to changes in the concentration in the surrounding tissue and liquid. This is because a larger membrane area is available for permeation into the measurement volume and because the required diffusion length of the compound in the measurement volume can be shorter than the optical path length. The measurement volume can be filled with liquid or with a solid matrix permeable to a compound to be analysed.

The detected signal of the device is calibrated to a known concentration of the compound to be analysed, either one time for all or preferably from time to time. Measuring the concentration in a sample, taken at the same time as the optical measurement, can be used to achieve this calibration. The device however can be made self-calibrating, if two measurement volumes contain a known concentration of compound.

Figure 7:
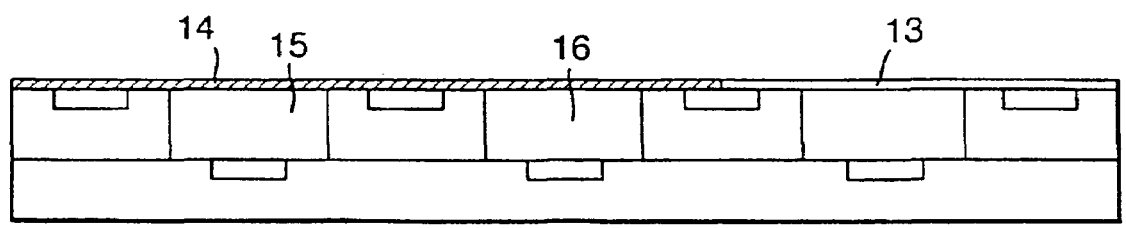
FIG. 7 is a schematic representation of a sixth implantable device embodying the invention, the device having detection areas covered partly by a membrane and partly by a lid on the top.

In FIG. 7 a part of the device is covered with a diffusion proof lid 14 instead of with a membrane. This forms two measurement volumes 15, 16 with known concentrations of the compound under analysis, preferably one volume with a concentration in the lower end and one volume with a concentration in the high end of the required measurement range.

The formation of a bio film on the implanted device will have less effect than is the case for electrochemical devices or other devices in which the compound to be measured is consumed in the measurement process. As long as the bio film is sufficiently transparent at the optical wavelengths employed, the bio film will have very little effect on the measurement. In the case where a membrane is used, as described above, the bio film may influence the response time with respect to changes in the concentration in the surrounding tissue and liquid, but is will still have little effect on the measurement itself.

The two levels of detection areas can be increased to three or more different levels. By increasing from two to three or more levels, the dynamic range of the sensor can be increased, as the analysis of the detected signal then discloses three or more levels corresponding to 2 or more interaction volume optical path lengths. Also more information is made available for data analysis to establish compound concentrations using, for example, chemometric, multivariant data analysis approaches. More levels also facilitate consistency and quality control of data.

Figure 9:
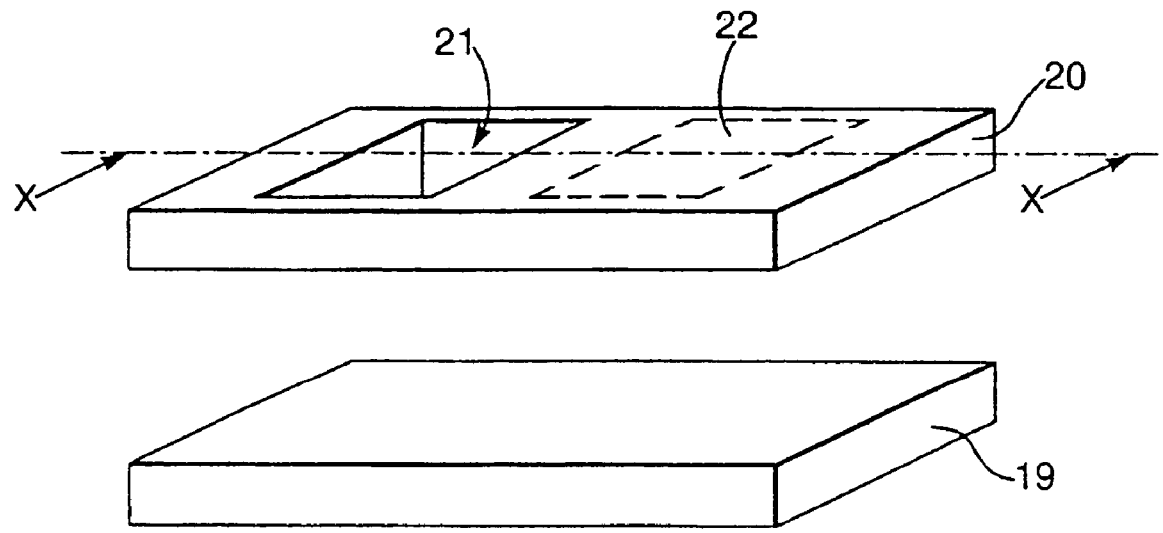
FIG. 9 is a schematic representation of an eighth implantable device embodying the invention the device including a spacer covering some of the areas of the device.

Turning now to FIG. 9, the implanted device is shown made as a laminated structure, where a base plate 19 contains the detectors, the wiring and an electronic circuit device. The top part 20 is laminated on the base plate, whereafter the base plate and the top part together forms the implantable device.

Figure 10:
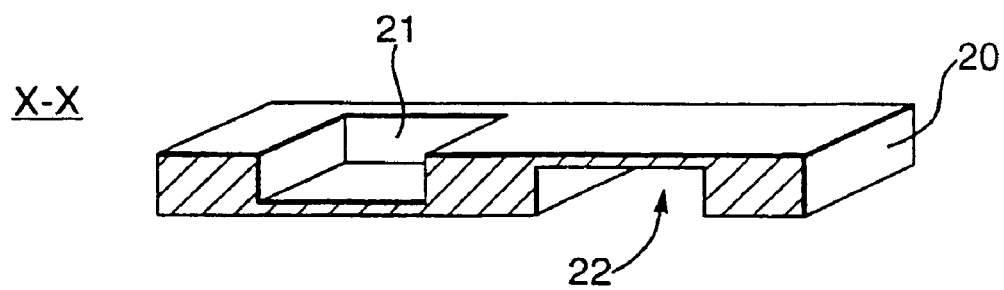
FIG. 10 shows a section through FIG. 9 along the line X-X and shows the spacer.

In the top part 20 two spaces 21 and 22 are made, simply by removing some material from the top part 20. The two spaces form two areas so that the device is able to detect light from two areas. The space 21 is created on the surface of the top part which faces away from the base plate so that compounds and tissue have access to the space when the device is implanted. The space 22 however is formed on the surface of the top part which faces towards the base plate so that compounds and tissue have no access to the space 22 when the device is implanted, as the space 22 is closed. This is indicated in FIG. 10, showing a section through X-X of the top part of FIG. 9. The detecting area underneath space 21 and space 22 is formed on the same surface but as the space 22 is closed, the interaction of light with compounds and tissue occurs over a larger distance at space 21 than at space 22. The closed space 22 forms a spacer. A spacer can also be formed of a solid material transparent to the incident light. A "spacer" is to be understood as a volume in which no interaction of light with compounds and tissue occurs.

Instead of operating with transmitted light received by photo detectors, the photo detectors can be replaced by reflectors to reflect light back to external photo detectors for analysis.

The invention claimed is:

1. A device for implantation beneath the skin of a living creature, the device having outer surfaces of biocompatible material and comprising:
    detection means for detection of light transmitted through the skin, said detection means comprising: at least one substantially flat first area including a first photodetector, and at least one substantially flat second area including a second photodetector, the arrangement of the first and second areas being such that light transmitted through the skin to the device interacts with compounds and tissues over a different distance between the skin and the first area than between the skin and the second area; and
    transmitting means for transmitting signals derived from said detection means to an external device.

2. The device according to claim 1, wherein the detection means includes first and second groups of corresponding first and second areas the first group of areas forms a common first level, the second group of areas forms a common second level, and the common first and second levels have a predetermined spacing from each other to provide the difference in distance over which light interacts with compounds and tissue between the skin and the first and second areas.

3. The device according to claim 2, wherein the first group of areas is formed at a base level of the device and the second group of areas is formed by projections from the said base level to a top level.

4. The device according to claim 3, wherein the detection means further includes at least one substantially flat third area including a third photodetector, forming a common level between the base level and the top level.

5. The device according to claim 1, further including a spacer, covering at least one second area so that compounds and tissue are unable to fill a volume defined between the spacer and the at least one second area, the volume between the spacer and the at least one second area providing the difference in distance over which light interacts with compounds and tissue.

6. The device according to claim 1, wherein at least a part of one of said first and second areas is covered by a permeable membrane.

7. The device according to claim 6, wherein the membrane is permeable to glucose.

8. A method for optically detecting the content of a compound in the body of a living creature, the method comprising:
    directing an external light source on different areas of an implanted device containing detection means, the distance, between the skin and said detection means, over which light from the light source interacts with compounds and tissue in respect of one area differing from the distance, between the skin and said detection means, over which light from the light source interacts with compounds and tissue in respect of another area;
    obtaining light-representing signals representing the light directed at the different areas of said detection means; and
    obtaining a value for the content of the compound by analysing the light-representing signals, the analysis being based on the difference between the light-representing signals from the different areas of the detection means.

9. The method according to claim 8, wherein the compound is glucose.

10. The method according to claim 8, wherein the value obtained is at least temporarily stored.

11. A method for optically detecting the content of a compound in the body of a living creature, the method comprising:
    directing an external light source on different areas of an implanted device containing detection means;
    obtaining light-representing signals by means of said detection means;
    transmitting said light-representing signals to an external device; and
    obtaining a value for the content of the compound by analysing the light-representing signals, the analysis being based on the difference between the light-representing signals from the different areas of the detection means.

12. The method according to claim 11, wherein the compound is glucose.

13. The method according to claim 11, wherein the value obtained is at least temporarily stored.

14. A subcutaneous implant comprising:

an implant body having a first and a second level;

a first and a second light detector arranged, respectively, at the first and second levels, and facing in a substantially similar direction; and transmitting means for transmitting a signal derived from the light detectors to an external device;

wherein the first and second levels are separated in the direction the first and second light detectors are facing, such that light propagating from an external source toward the implant body with substantially perpendicular incidence to the first and second light detectors must travel a longer distance to reach the first light detector than the second light detector.

15. The implant of claim 14, wherein the first and second light detectors are arranged in first and second light wells defined, respectively, within the first and second levels.

16. The implant of claim 14, wherein the first and second light detectors are arranged on substantially flat services formed at their respective levels.

17. The implant of claim 14, further comprising:

a third light detector arranged at the first level, a first calibration volume above the third light detector extending to the level of the second light detector being surrounded by a portion of the implant body;

a first diffusion-proof lid covering the first calibration volume above the third light detector, the first diffusion-proof lid being transparent to the light from the external light source; and a first medium having a known concentration of a compound located in the first calibration volume above the third light detector.

18. The implant of claim 17, further comprising:

a fourth light detector arranged at the first level, a second calibration volume above the fourth light detector extending to the level of the second light detector being surrounded by another portion of the implant body;

a second diffusion-proof lid covering the second calibration volume above the fourth light detector, the second diffusion-proof lid being transparent to the light from the external light source; and a second medium having a known concentration of a compound located in the second calibration volume above the fourth light detector;

wherein the concentrations in the first and second medium correspond, respectively, to upper and lower ends of a required measurement range for the compound.

19. A subcutaneous implant comprising:

a base;

a first and a second light detector arranged on the base facing in substantially the same direction;

a spacer mounted on the base over the second light detector, the spacer being transparent to light from an external light source and defining a volume in which no interaction of light with tissues and compounds occurs; and transmitting means for transmitting a signal derived from the light detectors to an external device;

wherein, with the implant implanted under the skin such that the first and second light detectors are a substantially equal distance from the skin, the light from the external light source interacts with compounds and tissues over a longer distance before reaching the first light detector than the second light detector, due, at least in part, to the volume defined by the spacer.

20. The implant of claim 19, wherein the spacer is included in a top plate mounted on the base, the volume being formed by a recess in the top plate.

\* \* \* \* \*